United States Patent [19]
Kuroda

[11] Patent Number: 4,971,917
[45] Date of Patent: Nov. 20, 1990

[54] REAGENT FOR RETICULOCYTE COUNTING BY FLOW CYTOMETRY

[75] Inventor: Tomoyuki Kuroda, Kakogawa, Japan

[73] Assignee: Toa Medical Electronics Co., Ltd., Kobe, Japan

[21] Appl. No.: 117,024

[22] Filed: Nov. 4, 1987

[30] Foreign Application Priority Data

Jul. 31, 1987 [JP] Japan .................................. 62-192414

[51] Int. Cl.$^5$ ..................... G01N 21/76; G01N 33/48; G01N 33/554; G01N 33/555
[52] U.S. Cl. ......................................... 436/63; 436/56; 436/172; 436/519; 436/520
[58] Field of Search .................. 436/63, 172, 519, 520, 436/56, 546; 435/2, 4, 7, 35, 34

[56] References Cited

U.S. PATENT DOCUMENTS

| | | | |
|---|---|---|---|
| 3,890,099 | 6/1975 | Jung | 422/68 |
| 4,193,980 | 3/1980 | Clason et al. | 436/63 |
| 4,208,479 | 6/1980 | Zuk et al. | 436/512 |
| 4,220,450 | 9/1980 | Maggio | 436/500 |
| 4,336,029 | 6/1982 | Natale | 436/172 |
| 4,801,549 | 1/1989 | Cremins et al. | 436/63 |

*Primary Examiner*—Robert J. Warden
*Assistant Examiner*—Kimberly A. Trautman
*Attorney, Agent, or Firm*—Fitch, Evan, Tabin & Flannery

[57] ABSTRACT

A reagent for reticulocyte counting by flow cytometry characterized in that it contains a carbonate salt.

If a blood sample is left exposed to ordinary air, non-specific staining of erythrocyte can be prevented with the addition of not less than about 1 mM of NaHCO$_3$.

7 Claims, 4 Drawing Sheets

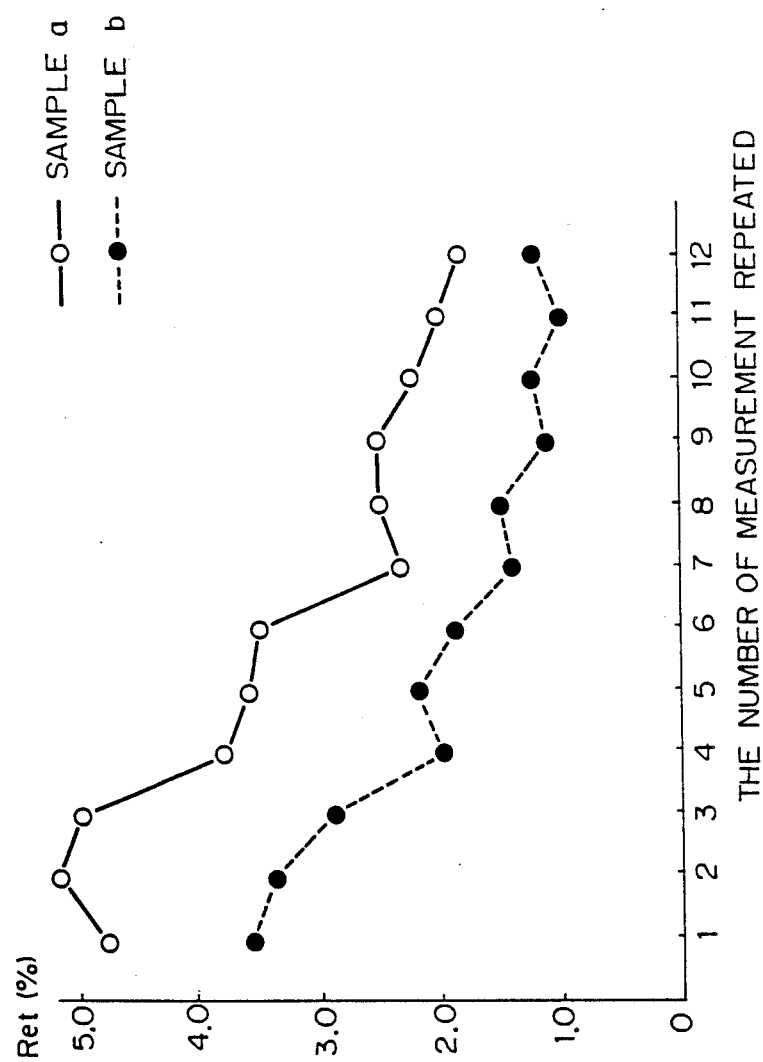

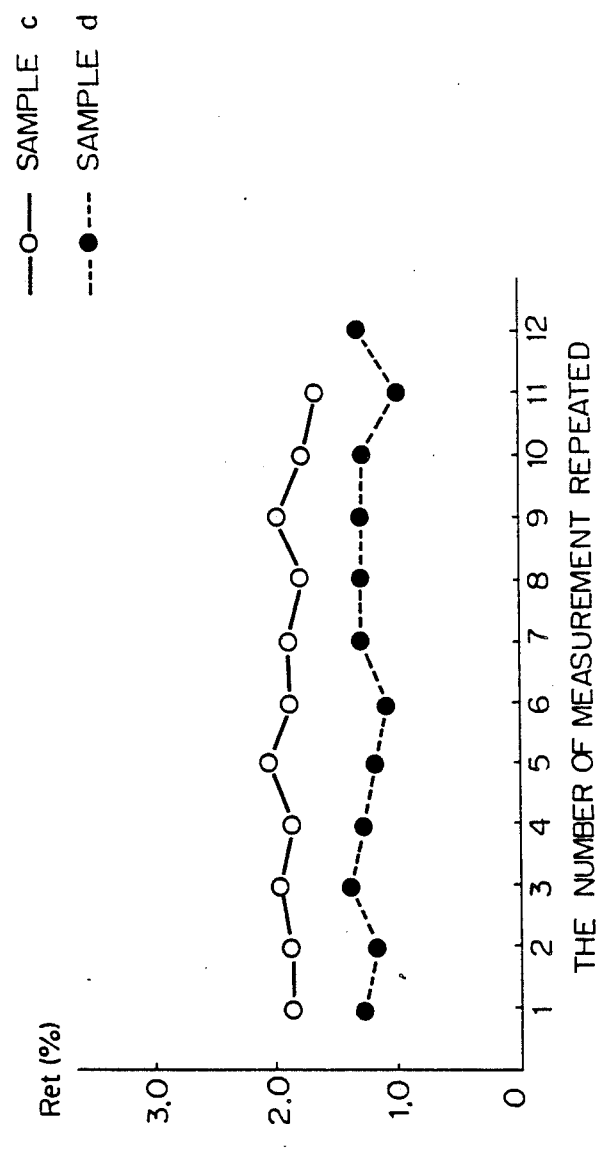

REAGENT FOR RETICULOCYTE COUNTING BY FLOW CYTOMETRY

The present invention relates to a reagent for reticulocyte counting by flow cytometry. More particularly, the present invention relates to such a reagent characterized in that it contains a carbonate salt.

BACKGROUND OF THE INVENTION

Immature erythrocytes in the blood are called reticulocytes, and normally account for 0.7–2.2% of the total count of erythrocytes. Determination of reticulocyte count helps confirmation of the diagnosis of such diseases as acute internal hemorrhage, hemolytic anemia, aplastic anemia, etc., and also helps in monitoring the progress of a patient's conditions after drug administration; thus it is regarded as being very important in the field of clinical laboratory tests.

A method which has been employed for the counting of said reticulocytes is conducted as follows: a smear of blood sample stained with a basic dye such as new methylene blue, brilliant cresyl blue, etc. is observed and the percentage of the count of stained reticulocytes is determined with respect to the total erythrocyte count.

This method requires a lot of time and involves a considerable workload for pre-treatment of blood samples, e.g. staining, etc., and as well as for visual counting after staining, and is inappropriate when the number of samples is large.

Therefore, many methods have been proposed in which reticulocyte counting is automated by the application of flow cytometry. For example, methods in which a fluorochrome reagent containing Auramine O is used for counting reticulocytes by flow cytometry are disclosed in Japanese Patent Public Disclosure No. 280565/1986 and Japanese Patent Public Disclosure No. 34058/1987.

The present inventors conducted reticulocyte counting by flow cytometry in the following way using a reagent of the composition shown below as an example of a staining solution, in order to examine the effects of Auramine O described in the aforementioned prior literature, Japanese Patent Public Disclosure No. 280565/1986 and Japanese Patent Public Disclosure No. 34058/1987:

| | |
|---|---|
| Auramino O | 500 ppm |
| ethylene glycol | 2.5 v/v % |
| HEPES · sodium hydroxide | 20 mM |
| N-2-hydroxyethylpiperazine-N'-2 ethane sulfonic acid | |
| NaCl | 120 mM |

The measurement was conducted 12 times continuously for each blood sample using a flow cytometry apparatus which was turned to have an appropriate degree of sensitivity. About 20 seconds before each measurement, the blood sample vessel containing the blood sample was repeatedly turned upside down for the purpose of stirring it. The blood sample vessel was opened and 400 $\mu$l of the blood sample inside was aspirated immediately before each measurement.

FIG. 1 shows the measurement results for two samples. Both of the samples showed decrease in reticulocyte count (Ret%) as the measurements were repeated. Under conditions like this, accurate reticulocyte counting cannot be expected.

In the above-mentioned measurements, the value of blood required each time was as large as 400 $\mu$l because a fully automated flow cytometry apparatus was used. If, however, the blood sample is subjected to flow cytometry after being stained manually, only about 10 $\mu$l of blood is necessary. In cases where blood is aspirated by 10 $\mu$l a notable change in reticulocyte count (%) such as that observed in FIG. 1 does not occur. Even if non-specific staining occurs and the fluorescence intensity increases as a whole, an almost completely accurate reticulocyte count (%) will be recorded as long as the sensitivity of the apparatus is controlled appropriately for that condition.

In other words, non-specific staining occurs only when a continuous measurement is made with a sample by aspirating a large volume of blood from the same sample each time.

BRIEF DESCRIPTION OF THE DRAWINGS

FIG. 1 shows the results of a continuous reticulocyte counting using an Auramine O staining reagent with a composition of the prior art; the abscissa denotes the reticulocyte count (%), and the ordinate the number of measurement repeated.

FIG. 3 shows the results of a continuous counting of reticulocytes using the reagent (ii) in Table 1; its abscissa and ordinate denote the same as those in FIG. 1.

DETAILED DESCRIPTION OF THE INVENTION

Figure 2A:
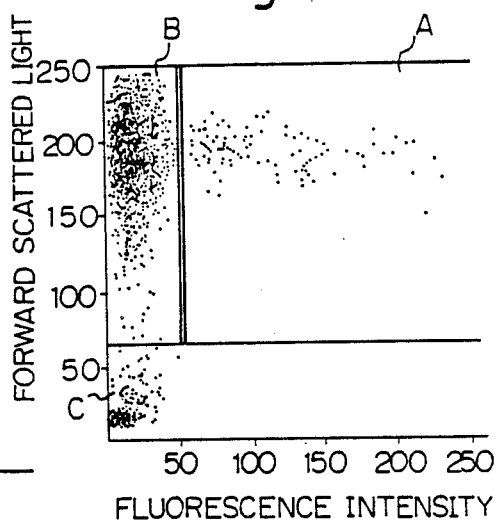
FIGS. 2(a), 2(b) and 2(c) show respectively the results of reticulocyte counting by flow cytometry using the Auramine O staining solution of the present invention with the following blood samples which were stored for a certain time before measurement in three different ways: a blood sample stored in a sample vessel tightly sealed, a sample exposed to the air in an uncapped sample vessel, and a sample exposed to $CO_2$ atmosphere in an uncapped sample vessel. A in the figures represents an area corresponding to reticulocytes, B an area corresponding to mature erythrocytes, and C an area corresponding to platelets.
Figure 2B:
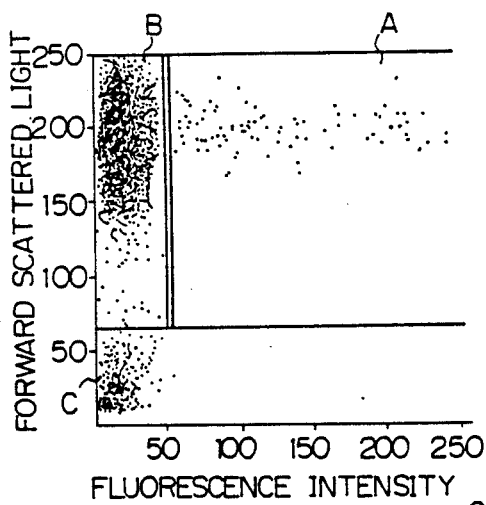
Figure 2C:
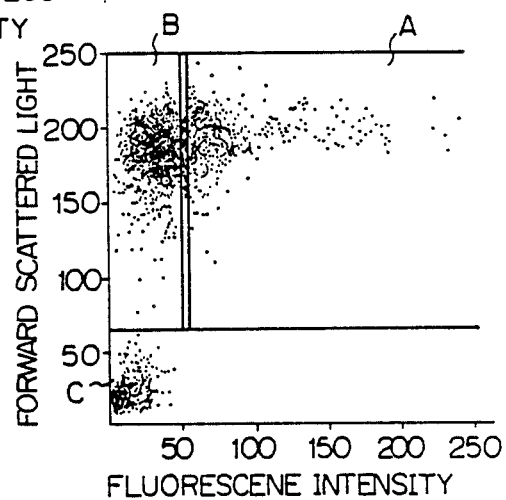

In order to clarify further the above-mentioned problem of non-specific staining, the following experiment was conducted. A single sample was divided into three: the first part of the sample was stored in a sample vessel that was tightly sealed; the second part of the sample was exposed to the air with the uncapped vessel; and the third part of the sample was exposed to a $CO_2$ atmosphere by placing it in an open vessel in a $CO_2$ environment. After a certain time had elapsed reticulocyte counting was conducted with each specimen using the said Auramine O staining solution by flow cytometry. The results are shown in FIGS. 2(a), 2(b) and 2(c).

In each figure, the abscissa represents the relative intensity of fluorescence, the ordinate the relative intensity of forward scattered light, and each point represents each cell counted. A in the figures represents an area corresponding to reticulocytes, B an area corresponding to mature erythrocytes, and C an area corresponding to platelets. FIG. 2(a) shows the result when the blood sample was tightly sealed within a sample vessel, FIG. 2(b) the result when the sample was exposed to the air, and FIG. 2(c) the result when the sample was exposed to a $CO_2$ atmosphere. The number of cells counted in the area A corresponding to reticulocytes was 164 in the case of FIG. 2(a), 145 in the case of FIG. 2(b), and 2579 in the case of FIG. 2(c). It can be seen that in the case of FIG. 2(c), mature erythrocytes are dyed (non-specific staining) as well, and thus are erroneously counted as reticulocytes.

The causes of the above-mentioned phenomena and problems can be explained as follows:

In general, $HCO_3^-$ and $CO_2$ are present in erythrocytes. These $HCO_3^-$ and $CO_2$ within erythrocytes are in equilibrium with negative ions in blood (plasma). Hereinafter both $HCO_3^-$ and $CO_2$ are collectively referred to as $CO_2$.

If the $CO_2$ concentration in the plasma changes, the $CO_2$ concentration in erythrocytes changes in the same direction. The $CO_2$ concentration in the plasma is in equilibrium with the $CO_2$ in the environment in which the blood is placed, and the $CO_2$ concentration in the plasma changes in the same direction as that of the $CO_2$ concentration in the environment. Therefore, erythrocytes left in an atmosphere abundant in $CO_2$ will become abundant in $CO_2$, and the $CO_2$ in erythrocytes in a blood sample stored tightly sealed in the air, and which contains little $CO_2$ ($CO_2$ concentration: 0.03%), will decrease.

Erythrocytes present in a staining solution will undergo an ion exchange reaction similar to that described above. This situation can be analyzed as follows:

(A) The amount of $CO_2$ contained in the staining solution is larger than that in erythrocytes.

In this case, the amount of $CO_2$ in the erythrocytes will increase.

(B) The amount of $CO_2$ in the staining solution is smaller than that in erythrocytes.

In this case, the amount of $CO_2$ in the erythrocytes will decrease, and will be exchanged with other anions in the staining solution.

The above category (B) may be further divided into two:

(B-1) The case in which the staining solution contains halogen anions such as $Cl^-$, etc.

In this case, the amount of halogen ions in the erythrocytes will increase.

(B-2) The case in which the staining solution does not contain halogen ions.

In this case, the amount of halogen ions in the erythrocytes will not change and the amount of other anions will increase.

The amount of said halogen ions such as $Cl^-$ in the erythrocytes has a large influence on the forms of erythrocytes and the membrane-permeability of the dye. Therefore, in case (B-1) above, the tendency of dye uptake and the forms of erythrocytes will change.

In general, $CO_2$ concentration in the air is lower than that in blood corpuscles. Therefore, when the blood is exposed to the atmosphere, $CO_2$ will move from erythrocytes to the air. When the blood is stored in a tightly-sealed vessel, $CO_2$ will move from erythrocytes to the air until a certain equilibrium is reached. If the vessel is opened during storage, the air within the vessel will be exchanged and $CO_2$ will move from the erythrocytes to the air again. If a specified amount of blood is aspirated each time the vessel is opened, the volume of blood within the vessel will be decreased accordingly, and the amount of air in the vessel will increase, which will result in conditions essentially similar to those in the case of blood contained in a vessel open to the air. Therefore, the $CO_2$ concentration in erythrocytes will decrease to the subsistence in the case when the blood is exposed to air.

In the case of a reagent shown in the aforementioned FIG. 1, 400 $\mu$l of blood was aspirated each time the tightly-sealed sample vessel was opened and subjected to flow cytometry for counting. About 10 ml of blood contained at first in the sample vessel decreased rapidly during this process, and the amount of $CO_2$ in erythrocytes is speculated to have decreased rapidly also. If the blood in which the $CO_2$ amount in erythrocytes is decreased as described above is stained with the above-mentioned Auramine O staining solution, $CO_2$ moves from the staining solution to the erythrocytes, but any halogen ions in the staining solution do not move to the erythrocytes.

On the other hand, however, the amount of $CO_2$ in the erythrocytes which were present in the original blood placed in the sample vessel was much larger than the amount of $CO_2$ in the staining solution, and if the corpuscles in this blood were stained with the Auramine O staining solution, the $CO_2$ would move from erythrocytes to the staining solution. At this time, the halogen ions in the staining solution would move to the erythrocytes in exchange with $CO_2$. The Auramine 0 staining solution contains $Cl^-$ ions, and these $Cl^-$ ions move to the erythrocytes. Namely, this will correspond to the above-mentioned case (B-1).

As described above, when $Cl^-$ ions are abundant in erythrocytes, mature erythrocytes will be stained (non-specific staining) in addition to the reticulocytes which are supposed to be specifically stained. Therefore, some of the mature erythrocytes are counted erroneously as reticulocytes in flow cytometry. It is for this reason that the reticulocyte counts in earlier measurements are anomalously high in FIG. 1. As the measurements are repeated, the reticulocyte counts will be stabilized and reach normal values.

Also, as is shown in FIG. 2(c), in the case in which blood is exposed to a $CO_2$ atmosphere, a large amount of $CO_2$ moves to the erythrocytes. When the erythrocytes are stained with the staining solution, a large amount of $CO_2$ in the erythrocytes moves to the staining solution, and a large amount of $Cl^-$ ions move from the staining solution to the erythrocytes. The fluorochrome moves to the erythrocytes in accordance with the movement of $Cl^-$. Therefore, a non-specific staining of erythrocytes occurs intensely and the number of erythrocytes counted erroneously as reticulocytes increases anomalously. Furthermore, the forward scattered light distribution is changed in FIG. 2(c); this is because of the change in erythrocyte forms.

The aforementioned non-specific staining results from the change in the amount of fluorochrome taken into mature erythrocytes or the amount of the same attached to the erythrocyte membrane.

The degree of non-specific staining changes from specimen to specimen. This is because the amount of $CO_2$ in erythrocytes differs from person to person, and the amount of $CO_2$ is related to the maintenance of blood pH (normally, 7.4).

The above-mentioned problem is observed not only with Auramine O staining solutions but also with all dyes which are used for this type of biological staining.

Therefore, the present invention provides a reagent for reticulocyte counting by flow cytometry which is characterized in that it contains a carbonate salt.

The carbonate salt is one that can provide $HCO_3^-$ in an aqueous medium and preferably $NaHCO_3$.

The concentration of the carbonate salt in the reagent is preferably 1-300 mM.

By making the $CO_2$ content in a staining solution larger than that in erythrocytes, $CO_2$ moves from the staining solution to erythrocytes when corpuscles in the blood are stained with the staining solution. In this case, any halogen ions in the staining solution do not move to erythrocytes. Additionally, since the halogen ions originally present in the erythrocytes move to the staining solution, non-specific staining, the extent of which largely depends on the environment in which the erythrocytes are left before measurement, does not occur.

The present invention is illustrated further by the following examples.

Example 1

Counting was conducted with reagents of the 7 different compositions shown in Table 1.

The reagent denoted as (i) is a conventional one. In the reagent (ii), the NaCl content was decreased to half of that in the conventional one, and $NaHCO_3$ was added. In the reagent (iii), NaCl was completely removed from the conventional reagent, and $NaHCO_3$ was added. In the reagent (iv), NaCl was completely removed and the content of HEPES buffer solution was increased. In the reagent (v), NaCl was completely removed and NaBr was added. In the reagent (vi), NaCl was completely removed and $Na_2SO_4$ was added. In the reagent (vii), NaCl was completely removed and citric acid was added. In all of these reagents, the content of Auramine 0 was 400 ppm and the pH was 8.0.

The blood specimens were prepared from a common sample; one was exposed to the air and the other to $CO_2$ atmosphere. The results are shown on the right side of Table 1. MRBC in the Table denotes mature Red Blood Cell, MFI Mean Fluorescence (relative) Intensity, and FSc Forward Scattered Light (relative intensity).

When the reagent (i) with the conventional composition was used, the results with the specimen exposed to $CO_2$ atmosphere show abnormally high values of both MRBC-MFI and RET%, because of non-specific staining of erythrocytes, as was explained above. Similar results were obtained when the reagent (v) was used. This observation confirms that non-specific erythrocyte staining occurs when the staining solution does not contain $CO_2$ while containing halogen ions.

When reagents (iv), (vi) and (vii) were used, staining was not successful and reticulocytes could not be counted. In cases with reagents (ii) and (iii), to which carbonate ions were added, non-specific staining of erythrocyte did not occur and normal reticulocyte counts were obtained even with the specimen which had been exposed to $CO_2$.

FIG. 3 shows the results obtained using the reagent (ii) with a single specimen measured continuously as in the case of the measurement shown in FIG. 1 the reticulocyte count (%) showed almost constant values.

Example 2

Figure 4:
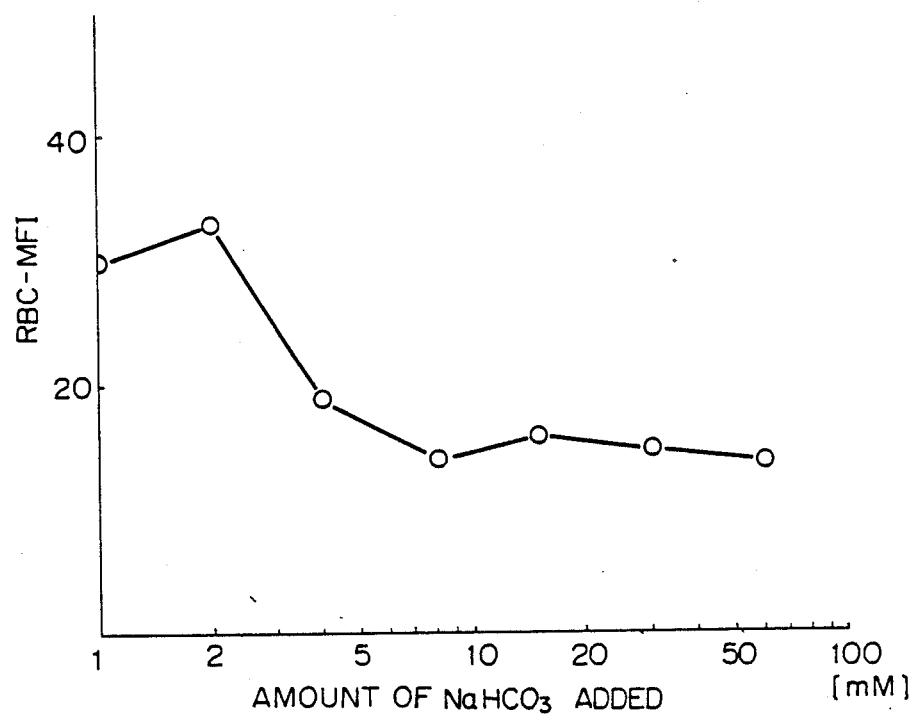
FIG. 4 shows the results of counting with a sample exposed to $CO_2$ atmosphere using the staining solution used in Example 2.

FIG. 4 shows the results of counting with a blood specimen exposed to $CO_2$ atmosphere and stained with a staining solution with the following composition:

| Composition of Staining Solution | |
| --- | --- |
| Auramino O | 400 μg/ml |
| Tris buffer solution | 20 mM |
| $NaHCO_3$ | 0-60 mM |
| NaCl | 60-120 mM |
| Ethylene glycol | 2% |
| pH | 8.5 |
| (Tricine was used for adjusting pH.) | |

The abscissa of FIG. 4 shows the amount of $NaHCO_3$ added, the ordinate RBC-MFI, i.e., red blood cell mean fluorescent (relative) intensity. When the amount of $NaHCO_3$ added is 0-2 mM, non-specific staining of erythrocyte occurs and RBC-MFI shows high values. When it is 4 mM, the values are still a little high and when it is 8-60 mM, the values are almost constant. From the results, if the amount of $NaHCO_3$ is not less than ca. 5 mM, the non-specific staining of erythrocytes can be prevented.

However, the results of Example 2 were obtained

TABLE 1

| Reagent No. | Composition of reagent | | | | Results | | | | | |
| --- | --- | --- | --- | --- | --- | --- | --- | --- | --- | --- |
| | HEPES (mM) | NaCl (mM) | $NaHCO_3$ (mM) | Others (mM) | Exposed to the air | | | Exposed to $CO_2$ | | |
| | | | | | RET % | MRBC-MFI | RBC-FSc | RET % | MRBC-MFI | RBC-FSc |
| (i) | 20 | 120 | | | 1.6 | 20 | 178 | 30.3 | 35 | 180 |
| (ii) | 20 | 60 | 60 | | 1.7 | 19 | 174 | 1.9 | 19 | 175 |
| (iii) | 20 | | 120 | | 2.0 | 20 | 173 | 2.1 | 19 | 174 |
| (iv) | 120 | | | | 0.2 | 12 | 174 | 0.2 | 13 | 174 |
| (v) | 20 | | | NaBr 120 | 1.5 | 19 | 177 | 29.8 | 34 | 176 |
| (vi) | 20 | | | $Na_2SO_4$ 80 | 0.2 | 13 | 177 | 0.1 | 13 | 159 |
| (vii) | | | | citric acid 60 | 0.1 | 12 | 177 | 0.2 | 13 | 177 |

In any of these reagents, the content of Auramine O is 400 ppm, and pH is 8.0 under extremely harsh conditions leaving the blood exposed to a $CO_2$ atmosphere: if a blood sample is left exposed to ordinary air, non-specific staining of erythrocyte can be prevented with the addition of not less than ca. 1 mM of $NaHCO_3$.

The maximum amount of $NaHCO_3$ that can be added is the amount which makes the osmotic pressure of the staining solution not larger than about twice the osmotic pressure of an isotonic solution, i.e., not more than 300 mM.

What is claimed is:

1. A reagent for staining reticulocytes for counting by flow cytometry comprising an aqueous solution of a carbonate salt and a dye which is capable of specifically staining reticulocytes.

2. A reagent according to claim 1 wherein the concentration of said carbonate salt in said aqueous solution is from about 1 mM to about 300 mM.

3. A reagent according to claim 1 in which the carbonate salt is $NaHCO_3$ or $Na_2CO_3$.

4. A reagent for staining reticulocytes for counting by flow cytometry according to claim 1, wherein said dye is a fluorescent dye.

5. A reagent for staining reticulocytes for counting by flow cytometry according to claim 4, wherein said fluorescent dye is auramine 0.

6. A reagent for staining reticulocytes for counting by flow cytometry according to claim 3 wherein said dye is auramine 0.

7. A reagent for staining reticulocytes for counting by flow cytometry according to claim 6 wherein the carbonate salt concentration is from about 1 mM to about 300 mM.

* * * * *

UNITED STATES PATENT AND TRADEMARK OFFICE
CERTIFICATE OF CORRECTION

PATENT NO. : 4,971,917

DATED : November 20, 1990

INVENTOR(S) : Kuroda

It is certified that error appears in the above-identified patent and that said Letters Patent is hereby corrected as shown below:

Column 3, line 11, change "$HCO_3$-" to --$HCO_3^-$--.

Column 3, line 12, change "$HCO_3$-" to --$HCO_3^-$--.

Column 3, line 14, change "$HCO_3$-" to --$HCO_3^-$--.

Column 3, line 43, change "Cl-" to --$Cl^-$--.

Column 3, line 51, change "Cl-" to --$Cl^-$--.

Column 4, line 27, change "Cl-" (both occurrences) to --$Cl^-$-- (both occurrences).

Column 4, line 30, change "Cl-" to --$Cl^-$--.

Column 4, line 45, change "Cl-" to --$Cl^-$--.

Column 4, line 48, change "Cl-" to --$Cl^-$--.

Column 5, line 1, change "$HCO_3$-" to --$HCO_3^-$--.

Column 6, line 5, after "FIG. 1" insert --.-- (period).

Column 6, line 15, change "Auramino" to --Auramine--.

UNITED STATES PATENT AND TRADEMARK OFFICE
CERTIFICATE OF CORRECTION

PATENT NO. : 4,971,917

DATED : November 20, 1990

INVENTOR(S) : Kuroda

It is certified that error appears in the above-identified patent and that said Letters Patent is hereby corrected as shown below:

Column 6, line 19, change "Ethlene" to --Ethylene--.

Column 6, line 31, change "ca." to --about--.

Column 6, line 50, change ":" to --;--.

Signed and Sealed this

Eighteenth Day of February, 1992

Attest:

HARRY F. MANBECK, JR.

Attesting Officer                Commissioner of Patents and Trademarks